(12) United States Patent
Spinello

(10) Patent No.: US 6,296,623 B2
(45) Date of Patent: Oct. 2, 2001

(54) DISPOSABLE NEEDLE AND ANESTHETIC CARRIER ASSEMBLY

(76) Inventor: Ronald P. Spinello, 4169 Sycamore La., Red Lion, PA (US) 17356

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/261,299

(22) Filed: Mar. 2, 1999

(51) Int. Cl.[7] ....................................... A61M 1/00
(52) U.S. Cl. ................................................. 604/118
(58) Field of Search ..................... 604/118, 131, 604/151, 152, 154, 207, 232, 148, 134; 433/28, 80, 82, 84, 85, 89

(56) References Cited

U.S. PATENT DOCUMENTS

| | | | |
|---|---|---|---|
| 4,430,079 | * | 2/1984 | Thill et al. . |
| 4,974,603 | * | 12/1990 | Jacobs . |
| 5,180,371 | * | 1/1993 | Spinello ........................ 604/118 |
| 5,354,537 | * | 10/1994 | Moreno . |
| 5,496,286 | * | 3/1996 | Stiehl et al. .................. 604/232 |
| 6,022,337 | * | 2/2000 | Herbst et al. ................. 604/131 |

* cited by examiner

Primary Examiner—Anhtuan T. Nguyen
Assistant Examiner—Ann Lam
(74) Attorney, Agent, or Firm—Galgano & Burke

(57) ABSTRACT

A disposable needle assembly having a holster for receiving and piercing a vial of anesthetic. The assembly is designed to facilitate the removal of the spent vial from the holster.

5 Claims, 1 Drawing Sheet

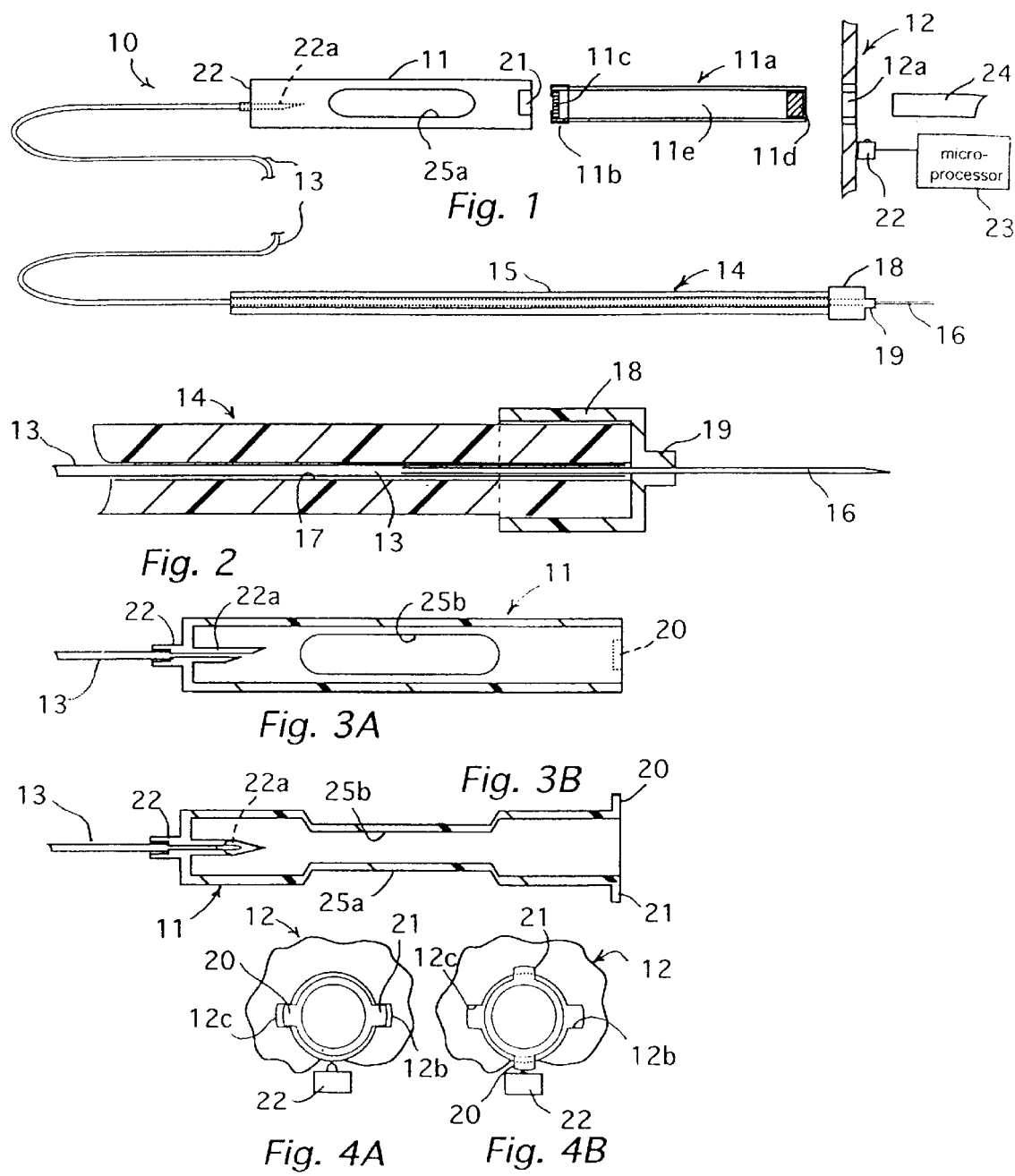

DISPOSABLE NEEDLE AND ANESTHETIC CARRIER ASSEMBLY

BACKGROUND OF THE INVENTION

1. Field of the Invention

The invention is a flexible conduit and carrier assembly for conveying liquid such as local anesthetic under elevated pressure from a vial to a hollow needle adapted to be implanted in the tissue, particularly the gingival tissue of the mouth.

2. Brief Discussion of the Related Art

The applicant's U.S. Pat. Nos. 4,747,824 and 5,180,371 disclose apparatus and method by means of which local anesthetic can be administered virtually without pain into the tissues, particular the mouth. In accordance with this invention, a vial of anesthetic is mounted in a holster unit detachably mounted at a programmed and controllable pumping station which forces the anesthetic from the vial at predetermined flow rates with greater precision than can be achieved with conventional hand syringes. The holster includes means to pierce the rubber diaphragm of the vial and to convey the liquid through a flexible microbore tube to a handle assembly carrying a conventional hollow needle to inject the anesthetic into the tissue.

Such holster, flexible conduit and needle assemblies must be disposable for sanitary reasons and must, therefore be relatively inexpensive. On the other hand, they must be engineered so they can quickly and easily be mated with anesthetic vials and then attached to the pumping station and just as easily be disassembled and not infrequently re-loaded for use on the same patient. They must also be light in weight, able to withstand high liquid pressures and readily manipulated at difficult injection sites.

The object of the invention, therefore, is to provide an assembly which meets all of these difficult and somewhat incompatible design criteria.

BRIEF DESCRIPTION OF THE PREFERRED EMBODIMENT OF THE INVENTION

In accordance with the invention, a holster design is provided which, as a single die cast unit, is capable of receiving a sealed vial of anesthetic and of automatically puncturing the membrane seal at the head end of the vial by means of an integral, sharp-pointed, hollow probe at the base of the holster to tap into the reservoir of liquid anesthetic. The holster includes tab means at its forward end to detachably lock it to the pumping station and to actuate a ram to drive the plug or piston in the rearward end of the vial into the vial's reservoir to force the liquid through the flexible microbore conduit to the needle under a wide range of pressures. The flexible conduit is coupled to both the holster and the needle handle in a high pressure seal.

Because it is frequently required that a second vial of anesthetic be used for the same patient, it should be possible to quickly detach the disposable assembly from the pump, eject the spent vial and insert a fresh vial. In accordance with the invention, swift removal of the spent vial is facilitated by arranging the geometry of the holster so that the vial can be gripped to detach it from the holster, when it is to be discarded. This can be achieved, for example, by means of a pair of complementary diametrically opposed finger apertures in the side wall of the holster to enable the vial to be tightly gripped and pulled out of the holster against the friction of the probe gripped by the rubber membrane of the vial.

DESCRIPTION OF THE DRAWINGS

FIG. 1 is a plan view of a holster, flexible conduit and needle assembly embodying the present invention, and also showing, disassembled, an anesthetic vial and a portion of a pumping station;

FIG. 2 is a view in longitudinal vertical section of the needle end of the handle portion;

FIG. 3A is a view in vertical longitudinal section of the holster portion of FIG. 1;

FIG. 3B is a view in horizontal longitudinal section of the holster portion of FIG. 1; and FIGS. 4A and 4B are two views in cross section showing the front end of the holster inserted in the pumping station, the latter showing the holster rotated 90° to engage the locking tabs and to start the microprocessor.

DESCRIPTION OF THE PREFERRED EMBODIMENTS

Referring to FIG. 1, the invention is shown as embodied in a disposable assembly 10 having an open-ended tubular holster 11 for receiving a vial or cartridge 11a, of anesthetic and for attachment to a programmed pumping station 12. The assembly 10 includes a flexible, microbore tube or conduit 13 coupled to a handle assembly 14 having a rigid elongated carrier 15, the free end of which is joined to a hollow needle 16 connected to the conduit 13 in fluid-tight relationship, as best seen in FIG. 2.

The flexible conduit 13 is threaded through a central bore 17 in the carrier 15 to receive the base end of the hollow needle 16. The needle is carried by a cap 18 having a needle sealing hub 19 and fitted over the free end of the carrier 15, also in sealing relationship. The pencil-like geometry of the handle assembly enables it to be held between the forefinger and the thumb of the doctor to enable the careful implantation of the needle in the most difficult injection sites.

The holster 11 as best seen in FIGS. 1, 3A and 3B is preferably cast in plastic as a unitary structure having a hollow cylindrical body to receive at its free or open end the charged anesthetic vial 11a, head or front end 11b first. The head end of a conventional anesthetic vial includes a penetrable rubber seal 11c held by a metal sealing ring while the back end is sealed by a plug or piston 11d which is slidable into the anesthetic reservoir 11e of the vial to drive the liquid forward.

The open or forward end of the holster 11 includes a pair of radially extending locking tabs 20 and 21 (best seen in FIGS. 3B and 4B) while the base or closed end is formed with a central, external hub 22 adapted to receive the flexible conduit 13 in sealing relationship. The base end is also formed internally with a hollow, molded, piercing probe 22A having a tip sharpened in at least three planes to define a piercing tip capable of penetration of the rubber seal 11c of the vial when it is inserted into the holster. Thus the flexible, microbore conduit 13 is connected to the anesthetic reservoir 11e.

With the vial 11a fully seated in the holster 11 with the probe 22a penetrating the rubber seal 11c, the assembly 10 is ready to be releasably locked to the pre-programmed pumping station 12. To this end, the wall of the pumping station is formed with a circular aperture 12a with diametrically opposed radial extensions 12b and 12c (best seen in FIG. 4B) to receive the radial tabs 20 and 21 of the holster. The holster is then rotated 90° counter-clockwise as viewed in FIGS. 4A and 4B to dispose the locking tabs behind the wall 12. At the same time the locking tab 20 rotates into engagement with a programming switch 22 connected to a microprocessor 23 in the pumping station 12 to actuate a plunger 24 to drive the plunger into the piston 11*d* in the vial 11*a*. The plunger is then controlled by the doctor and the micro-processor to complete the injection in accordance with the teaching of the applicant's aforesaid patents.

When the injection is completed (or the vial exhausted), the holster is then detached from the pumping station by reversing the insertion procedure. Removal of the vial from the holster requires that the rubber seal 11*c*, which is in tight frictional engagement with the piercing probe 22*a*, be readily detached from the probe. This is accomplished in accordance with the invention by forming in the holster diametrically opposed finger apertures 25*a* and 25*b* so that the vial within the holster can be tightly gripped with a force enabling the doctor or a technician to pull the vial away from the piercing probe in minimum time. A fresh cartridge or vial of anesthetic can then be inserted in the holster to provide for additional anesthetic to be injected into the same patient without any delay which would adversely affect the process. Alternatively, the geometry of the holster can be such that the length of the vial exceeds the length of the holster so that the end of the vial can be gripped when the holster is detached from the pumping station 12.

While the invention has been described above in reference to a preferred embodiment thereof, it will be understood that it can take other forms and arrangements. The invention should not, therefore, be regarded as limited except as set forward with the following claims.

What is claimed is:

1. A disposable needle handle and anesthetic carrier assembly for delivering liquid anesthetic under pressure into living tissues, the anesthetic being contained in disposable vials having an anesthetic reservoir between a piston at one end and a piercable self-sealing membrane at the other end through which the reservoir is tapped, the anesthetic being delivered by a pumping station having a movable plunger to engage the piston, the invention comprising:

an integrally cast plastic, holster at one end to receive the vial with its piston adjacent the open end;

wall means to confine the vial laterally in the holster;

a tubular hollow membrane piercing probe at the opposite end of the holster from the open end and formed integrally with the holster to engage and pierce the membrane of the vial, in tight frictional engagement therewith, and to be surrounded by the membrane in pressure sealing relationship; said hollow piercing-probe being circular in cross section with a circular hollow center and sharpened in at least three planes, each having a relatively steep angle to the axis of the probe, the first plane extending from one edge of the circle to a diametrically opposed point on the opposite edge, thereby to define an elliptically rounded tip on the probe, the other two planes intersecting each other and the peak of the rounded tip to define a point, said probe extending into the vial to cause the membrane to seal against the circular wall of the probe beyond the sharpened point; and a flexible microbore tube having one end coupled in pressure sealing relationship to the hollow tubular probe and the other end coupled in pressure sealing relationship to the needle at its handle;

said holster being substantially cylindrical to closely confine the vial, the geometry of the holster including aperture means to expose the vial to afford a frictional finger grip on the vial, whereby the vial can be pulled free of the circular wall of the integrally cast plastic piercing probe when the holster is detached from the pumping station.

2. A disposable needle handle and anesthetic carrier assembly as set forth in claim 1, said hollow piercing-probe being circular in cross section with a circular hollow center and sharpened in at least three planes, each having a relatively steep angle to the axis of the probe, the first plane extending from one edge of the circle to a diametrically opposed point on the opposite edge, thereby to define an elliptically rounded tip on the probe, the other two planes intersecting each other and the peak of the rounded tip to define a point.

3. A disposable needle handle and anesthetic carrier assembly as set forth in claim 1, said holster being substantially cylindrical to closely confine the vial, the geometry of the holster including aperture means to expose the vial.

4. A disposable needle handle and anesthetic carrier according to claim 1 comprising a pair of diametrically opposed apertures formed in the holster to expose the vial to be gripped by the fingers to be pulled free of the tight frictional engagement therewith.

5. A disposable needle handle and anesthetic carrier assembly according to claim 1 comprising control means in the pumping station to actuate the plunger and an apertured wall adjacent the plunger to receive the holster, locking tab means on the holster adjacent its open end to engage the apertured wall in locking relationship, and control means in the pumping station to be engaged by the tab means to actuate the plunger.

* * * * *